US010314668B2

(12) United States Patent
Bindayel

(10) Patent No.: US 10,314,668 B2
(45) Date of Patent: Jun. 11, 2019

(54) ORTHODONTIC SYSTEMS

(71) Applicant: Naif Bindayel, Riyadh (SA)

(72) Inventor: Naif Bindayel, Riyadh (SA)

( * ) Notice: Subject to any disclaimer, the term of this patent is extended or adjusted under 35 U.S.C. 154(b) by 200 days.

(21) Appl. No.: 15/160,277

(22) Filed: May 20, 2016

(65) Prior Publication Data
US 2017/0128166 A1 May 11, 2017

Related U.S. Application Data

(60) Provisional application No. 62/252,760, filed on Nov. 9, 2015.

(51) Int. Cl.
*A61C 7/20* (2006.01)
*A61B 90/98* (2016.01)
*A61C 7/00* (2006.01)
*A61C 7/12* (2006.01)
*A61C 7/14* (2006.01)
(Continued)

(52) U.S. Cl.
CPC ............ *A61B 90/98* (2016.02); *A61B 5/4547* (2013.01); *A61B 5/6802* (2013.01); *A61C 7/002* (2013.01); *A61C 7/12* (2013.01); *A61C 7/14* (2013.01); *A61C 7/20* (2013.01); *A61C 7/22* (2013.01); *A61C 7/28* (2013.01); *A61B 5/0022* (2013.01); *A61B 2090/064* (2016.02); *A61B 2560/0219* (2013.01); *A61B 2560/045* (2013.01); *A61B 2562/0252* (2013.01)

(58) Field of Classification Search
CPC ..... A61B 90/98; A61B 5/4547; A61B 5/6802; A61B 2090/064; A61B 5/0022; A61B 2560/0219; A61B 2560/045; A61B 2562/0252; A61C 7/002; A61C 7/12; A61C 7/14; A61C 7/20; A61C 7/22; A61C 7/28
See application file for complete search history.

(56) References Cited

U.S. PATENT DOCUMENTS 4,243,387 A 1/1981 Prins
4,292,025 A 9/1981 Förster
(Continued)

FOREIGN PATENT DOCUMENTS

WO  WO 03/096922  11/2003  ............... A61C 7/14

OTHER PUBLICATIONS

Machine translation of WO 03/096922 retreived from https://patentscope.wipo.int/search/en/detail.jsf?docId=WO2003096922&recNum=1&maxRec=&office=&prevFilter=&sortOption=&queryString=&tab=PCTDescription on Jul. 11, 2018.*
(Continued)

*Primary Examiner* — Heidi M Eide
(74) *Attorney, Agent, or Firm* — Fish & Richardson P.C.

(57) ABSTRACT

An orthodontic appliance includes a first orthodontic bracket having a first gear module, a second orthodontic bracket having a second gear module, and a first archwire segment having a first portion and a second portion. The first portion of the archwire segment is coupled to the first orthodontic bracket, the second portion of the archwire segment is coupled to the second orthodontic bracket. The first gear module is configured to provide a first force to the first portion of the first archwire segment, the second gear module is configured to provide a second force to the second portion of the first archwire segment, and the first gear module is configured to provide the first force independently of the second gear module.

76 Claims, 11 Drawing Sheets

(51) Int. Cl.
*A61C 7/22* (2006.01)
*A61C 7/28* (2006.01)
*A61B 5/00* (2006.01)
*A61B 90/00* (2016.01)

(56) References Cited

U.S. PATENT DOCUMENTS

| | | | |
|---|---|---|---|
| 5,032,080 | A | 7/1991 | Hakansson et al. |
| 5,035,614 | A | 7/1991 | Greenfield |
| 5,876,206 | A | 3/1999 | Maurer |
| 5,954,502 | A * | 9/1999 | Tuenge .......... A61C 7/14 433/16 |
| 6,632,088 | B2 | 10/2003 | Voudouris |
| 7,306,458 | B1 | 12/2007 | Lu |
| 7,581,714 | B2 | 9/2009 | Machu |
| 9,531,237 | B2 | 12/2016 | Miller |
| 2001/0029008 | A1 | 10/2001 | Jordan et al. |
| 2003/0031975 | A1 | 2/2003 | Voudouris |
| 2003/0152889 | A1 * | 8/2003 | Uji .......... A61C 13/0024 433/169 |
| 2005/0026102 | A1 | 2/2005 | Miller |
| 2005/0269821 | A1 | 12/2005 | Nadel et al. |
| 2006/0074431 | A1 | 4/2006 | Sutton et al. |
| 2007/0184399 | A1 | 8/2007 | Salich |
| 2008/0248439 | A1 | 10/2008 | Griffith et al. |
| 2009/0286195 | A1 | 11/2009 | Sears et al. |
| 2009/0317757 | A1 | 12/2009 | Lemchen |
| 2012/0148973 | A1 | 6/2012 | Johnston |
| 2014/0134562 | A1 | 5/2014 | Wu et al. |
| 2014/0272751 | A1 | 9/2014 | Cosse et al. |
| 2015/0305833 | A1 * | 10/2015 | Cosse .......... A61C 7/002 433/3 |

OTHER PUBLICATIONS

International Search Report and Written Opinion of the International Searching Authority for International Application No. PCT/IB2016/056759 dated Apr. 4, 2017.
Non-Final Office Action for U.S. Appl. No. 15/160,234 dated Apr. 10, 2017.
Non-Final Office Action for U.S. Appl. No. 15/160,255 dated Apr. 5, 2017.
Non-Final Office Action for U.S. Appl. No. 15/160,291 dated Apr. 7, 2017.
Non-Final Office Action for U.S. Appl. No. 15/160,337 dated May 23, 2018.
Final Office Action for U.S. Appl. No. 15/160,255 dated Aug. 29, 2017.
Non-Final Office Action for U.S. Appl. No. 15/160,291 dated Jun. 8, 2018.

* cited by examiner

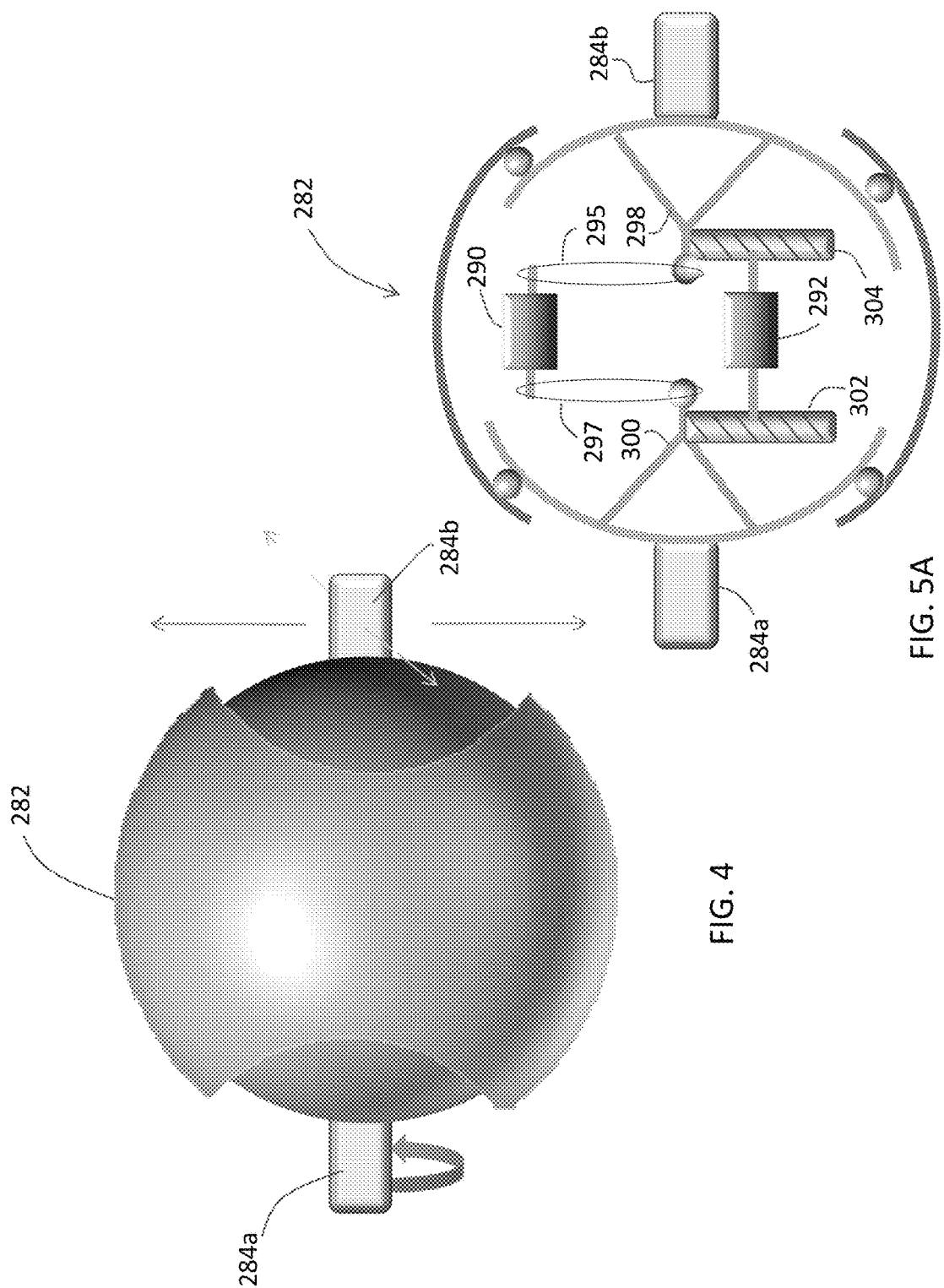

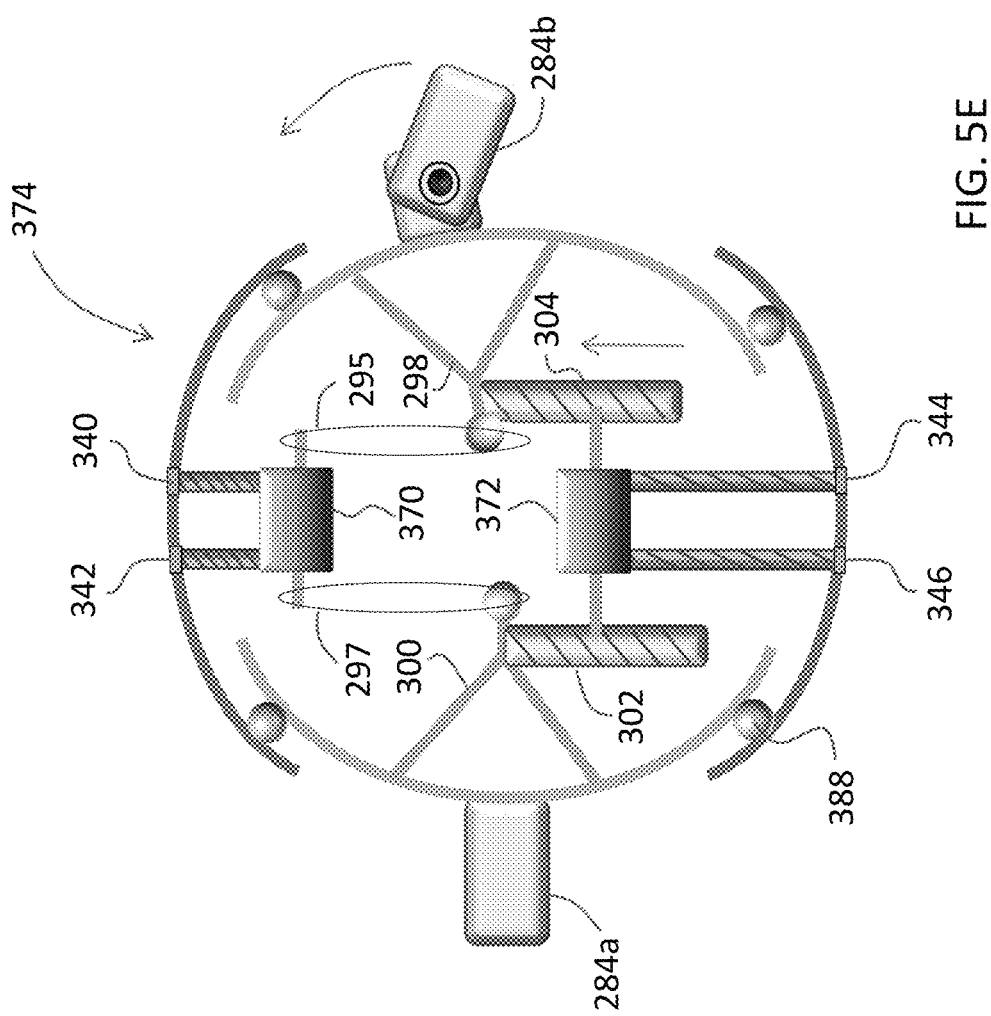

ORTHODONTIC SYSTEMS

CROSS-REFERENCE TO RELATED APPLICATIONS

This application claims priority to U.S. Provisional Patent Application 62/252,760, filed on Nov. 9, 2015. This application is related to U.S. patent application Ser. Nos. 15/160,275; 15/160,234; 15/160,291; 15/160,255; and Ser. No. 15/160,337. The contents of the above applications are incorporated by reference in their entirety.

TECHNICAL FIELD

This disclosure relates to orthodontic systems.

BACKGROUND

Orthodontic braces are useful in correcting alignment of teeth to proper positions and orientations in the dental arch and to improve dental health. In some examples, orthodontic braces include metal brackets bonded to the teeth and arch wires that are tied to the brackets by elastic ties. The arch wires are designed to apply force to the brackets and teeth, causing the teeth to slowly move or rotate in prescribed directions. The arch wires are adjusted, e.g., every three or four weeks during treatment to maintain pressure in order to supply prescribed forces to the teeth. There are many types of dental braces. For example, braces can be self-ligating such that the arch wire clips into the brackets without the need for ligatures. Some dental braces use computer-adjusted wires. These braces use the same principle of force delivery by an external source outside of the bracket (e.g., wire, coils, or elastics). In some examples, a bracket may have a base that is angulated to combine torque, angulation, in and out bend, and offsets for each tooth. This enables an unadjusted arch wire to perform variant alignment functions (i.e., with no further wire bending). In some examples, a series of clear molds may be used to produce teeth alignment. Orthodontic treatments generally last for two to three years.

SUMMARY

In a general aspect, an orthodontic appliance includes a first orthodontic bracket having a first gear module; a second orthodontic bracket having a second gear module; and a first archwire segment having a first portion and a second portion, the first portion being coupled to the first orthodontic bracket, the second portion being coupled to the second orthodontic bracket. The first gear module is configured to provide a first force to the first portion of the first archwire segment, the second gear module is configured to provide a second force to the second portion of the first archwire segment, and the first gear module is configured to provide the first force independently of the second gear module.

In another general aspect, an orthodontic appliance includes: a first orthodontic bracket (or node) configured to be attached to surfaces of two neighboring teeth, via twin archwire extensions; a second orthodontic bracket configured to be attached to surfaces of the following neighboring teeth via twin archwire extensions; an adjoining archwire segment sets in the middle between the two orthodontic brackets and having a first portion and a second portion, the first portion passing through the first and second orthodontics brackets to be driven by gear modules; the second portion connects the two brackets and engage to an intermediate conventional bracket attached to each tooth, each of the three gear modules generate a force that is applied to the second portion of the archwire segment independently.

In another general aspect, an orthodontic appliance includes a first module having a mesial end and a distal end; a second module having a mesial end and a distal end; a first archwire segment coupled to the distal end of the first module; a second archwire segment coupled between the mesial end of the first module and the distal end of the second module; and a third archwire segment coupled to the mesial end of the second module. The first and second modules have gear systems to move the second archwire segment relative to the first and second modules.

In a general aspect, an orthodontic appliance includes: a first orthodontic bracket (node) configured to be attached to the surfaces of two neighboring teeth, via its twin archwire extensions; a second orthodontic bracket configured to be attached to the surfaces of the following neighboring teeth via its twin archwire extensions; an adjoining archwire segment sets in the middle between each two orthodontic bracket with a first portion and a second portion, the first portion passing through the first and second orthodontics bracket to be fixed with a gear modules; the second portion connects the two brackets and engage to an intermediate conventional bracket attached to each tooth, each of the three gear modules can be driven to generate a force that is applied to the second portion of the archwire segment independently.

In another general aspect, a method for orthodontic treatment includes providing a first orthodontic bracket having a first gear module; providing a second orthodontic bracket having a second gear module; coupling a first portion of a first archwire segment to the first orthodontic bracket; coupling a second portion of the first archwire segment to the second orthodontic bracket; driving one or more gears in the first gear module to generate a first force that is applied to the first portion of the first archwire segment; and driving one or more gears in the second gear module to generate a second force that is applied to the second portion of the first archwire segment.

In another general aspect, a method for orthodontic treatment includes coupling a first archwire segment to a distal end of a first gear module; coupling a second archwire segment between a mesial end of the first gear module and a distal end of a second gear module; and coupling a third archwire segment to a mesial end of the second gear module; and driving gears in the first and second gear modules to apply forces to move the second archwire segment relative to the first and second gear modules.

In another general aspect, an orthodontic appliance includes an orthodontic node having a gear module; and a first archwire segment having a first end coupled to the orthodontic node. The gear module of the orthodontic node is configured to generate a first force that is applied to the first end of the first archwire segment.

Other aspects include other combinations of the features recited above and other features, expressed as methods, apparatus, systems, program products, and in other ways. Advantages of the aspects and implementations may include one or more of the following. The orthodontic brackets can be active brackets or smart brackets. A remote orthodontic system can allow active brackets or smart brackets to be remotely controlled or adjusted. The active brackets can generate force, and the force applied to the teeth can be increased or decreased while the patient is at home. The progress of teeth alignment can be monitored remotely. The remote orthodontic system can provide feedback and report symptoms, if any, to the orthodontist. In cases where adjustments to the original treatment plans are needed, the force adjustments can be made and applied while the patient is at home without the need to visit the dental clinic. The system can also provide an estimate of the remaining treatment time based on current progress of treatment. The system can reduce the trial and error in orthodontic treatment by using proper biomechanical pre-planning and insistent re-adjustment and monitoring. The system can improve the accessibility for orthodontic treatment in rural areas, and may reduce the number of days that school children miss classes. The orthodontic treatment outcomes may be more predictable, leading to a better quality with potentially reduced treatment side effects.

DESCRIPTION OF DRAWINGS

FIG. 4 is a diagram of an external front view of an exemplary smart node.

FIGS. 5A to 5D are diagrams of cross sectional views of the exemplary smart node along the longitudinal direction of the orthodontic wire.

FIG. 5E is a diagram of a cross sectional view of an exemplary smart node.

Like reference symbols in the various drawings indicate like elements.

DETAILED DESCRIPTION

This document describes an orthodontic system that enables an orthodontist to remotely monitor orthodontic braces on patients and make adjustments when necessary in a precise and predictable manner. In some implementations of the remote orthodontic system, the orthodontic system includes smart brackets in which each bracket has a miniature motor that drives a miniature gear, which in turn drives small rods or posts that push against an arch wire, generating a reaction force that pushes against the bracket's wings, in which the reaction force is transferred to the corresponding tooth to provide the required force for alignment of the tooth. The number of miniature motors and the configuration of the motor(s) can vary depending on design and functions. For example, the orthodontic system can include smart brackets in which each bracket has two miniature motors that drive miniature gears, which in turn pull or push an arch wire to generate opposing forces for alignment of the corresponding tooth (by generating couple forces system). In other implementations of the remote orthodontic system, the orthodontic system includes smart brackets in which each bracket has one or more miniature motors that drive one or more miniature gears, which in turn drive a rotatable base to provide root torque to the bracket for generating a force for alignment of the corresponding tooth. In some implementations of the remote orthodontic system, the orthodontic braces include arch wire segments connected by smart brackets in which each bracket has one or more miniature motors that apply forces to the arch wire segments, such that the combination of the forces generated by the plurality of brackets provide the proper amount of force for the alignment of each individual tooth.

Figure 1:
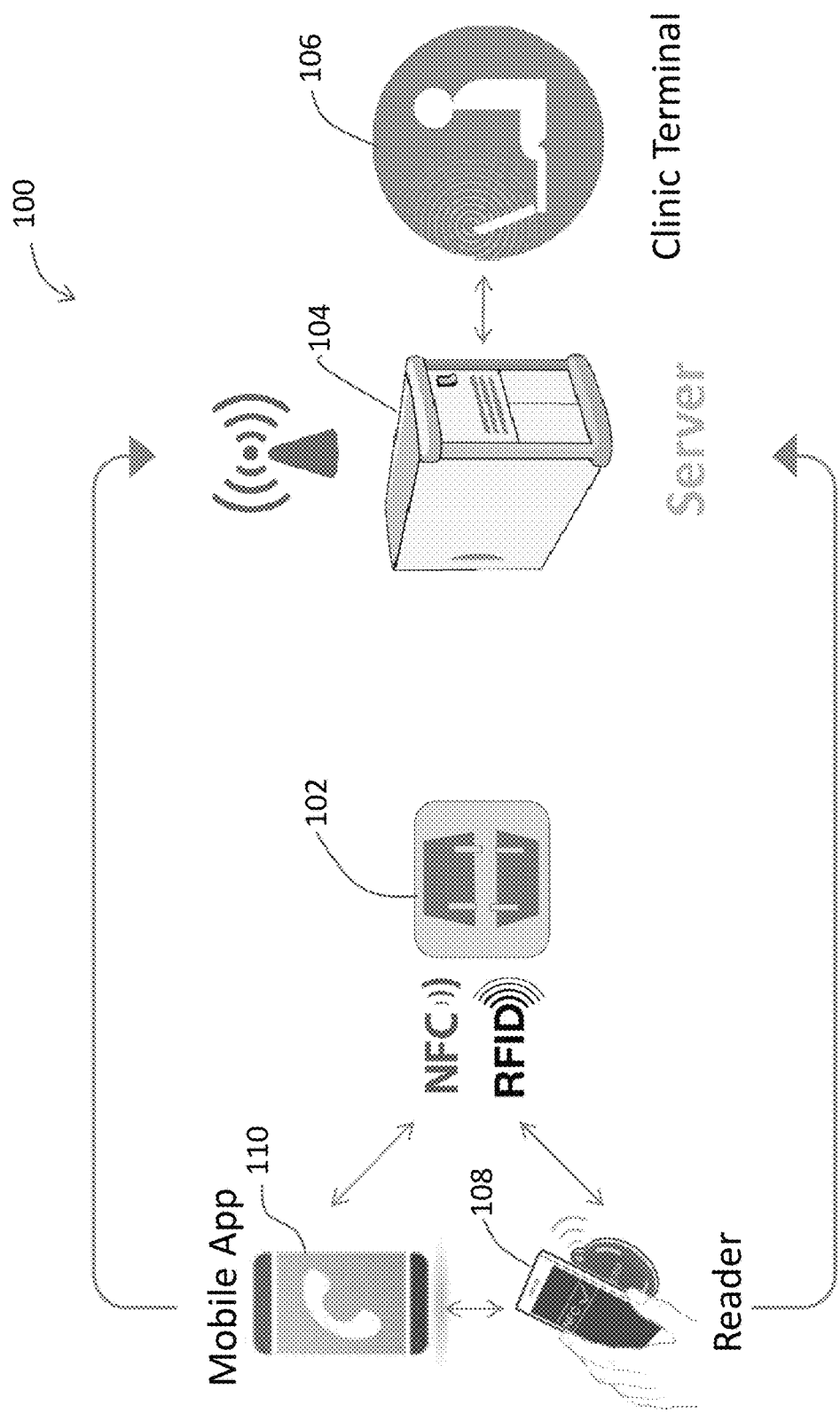
FIG. 1 is a diagram of an exemplary remote orthodontic system.

Referring to FIG. 1, a remote orthodontic system 100 includes orthodontic braces composed of smart brackets 102 (only one is shown in the figure) that communicate wirelessly with a computer server 104. The computer server 104 can be a physical machine located at the patient's home, or it can be a virtual server commonly referred to as a cloud server that resides remotely. The following describes examples in which the computer server 104 is a cloud server. In some examples, the computer server 104 may interact wirelessly with the brackets 102 by receiving signals from or sending signals to the brackets 102. This interaction occurs through, e.g., a home-based reader 108 or a user's cell phone 110, while the computer server 104 communicates with a clinic terminal 106 at a dental clinic. The computer server 104 receives signals from the brackets 102 (e.g., through the reader 108 or the cell phone 110), determines the current configurations of the brackets 102, determines whether adjustments are necessary, and sends back signals using the same route (e.g., through the reader 108 or the cell phone 110) to the brackets 102 in order to control motors in the brackets 102 to make the necessary adjustments. The computer server 104 communicates with the terminal 106 at the dental clinic to enable an orthodontist and/or other healthcare providers to monitor the configurations of the brackets 102 and enter commands to make additional adjustments when necessary.

In some implementations, when the patient first visits the orthodontist, the orthodontist may prescribe a treatment plan that specifies the amount and direction of force to be applied to each tooth at different time periods. The orthodontist may provide an electronic file that includes the treatment plan, and the patient may download, from the computer server 104, the electronic file having updated data containing the treatment plan to the reader 108 or the cell phone 110. The reader 108 or the cell phone 100 may execute an orthodontic application program that uses the information about the treatment plan to interact with the brackets 102.

After the first visit to the orthodontist, and at each follow up visit every three or four weeks, the orthodontist executes the orthodontic treatment program on the server 104. The orthodontic treatment program may analyze signals received from the brackets 102 to determine the progress of teeth alignment. The program may compare the current progress with the prescribed treatment plan and determine which brackets need to be adjusted to increase or decrease the force applied and its direction to the corresponding tooth, or to adjust the torque applied by the bracket to the tooth. The program instructs the server 104 to send signals to the brackets 102 to configure the brackets 102 such that each tooth receives the proper amount of force metrics according to the prescribed treatment plan.

Because the adjustments to the brackets 102 can be conveniently performed at the patient's home, the treatment plan may have instructions for more frequent bracket adjustments at finer time intervals, such as twice every month. The patient has the option of making adjustments to the brackets at times that are convenient to the patient.

The wireless reader 108 can interact wirelessly with the brackets 102 using a communication protocol similar to, e.g., the RFID protocol, Bluetooth protocol, or other protocols. The wireless reader 108 may be connected to the computer server 104 through a wire connection or a wireless link. The mobile phone 110 executing the orthodontic application program may interact wirelessly with the brackets 102 using a communication protocol similar to, e.g., the near-field communication protocol, Bluetooth protocol, or other protocols. The system may operate in, e.g., the 401-406 MHz, 902-928 MHz, 2400-2483.5 MHz, and/or 5725-5850 MHz bands. The mobile phone 110 may communicate with the computer server 104 through a wireless link.

In some implementations, the smart bracket 102 has sensors that can detect the amount of force (and/or the position trajectories) being applied to the tooth through the arch wire. Alternatively the sensors can be attached to or embedded in the arch wire itself. The sensors provide feedback signals so that the orthodontic treatment program executing on the computer server 104 can determine that the correct amount of force and the direction of force are applied to each tooth to ensure its proper alignment and positioning. If, after configuring the brackets 102, the sensors determine that the force/direction applied to the tooth deviates from the prescribed amount by more than a threshold value, the program may generate an alert signal, indicating that the patient should contact the orthodontist. Alternatively, the program can readjust and apply the new biomechanical force specifications. Upon receiving an instruction from the patient, the computer server 104 may send the data from the sensor to the clinic terminal 106 so that the orthodontist may determine whether it is possible to reconfigure the brackets remotely, or to inform the patient that it is necessary to return to the dental clinic for further examination and adjustment.

Figure 2:
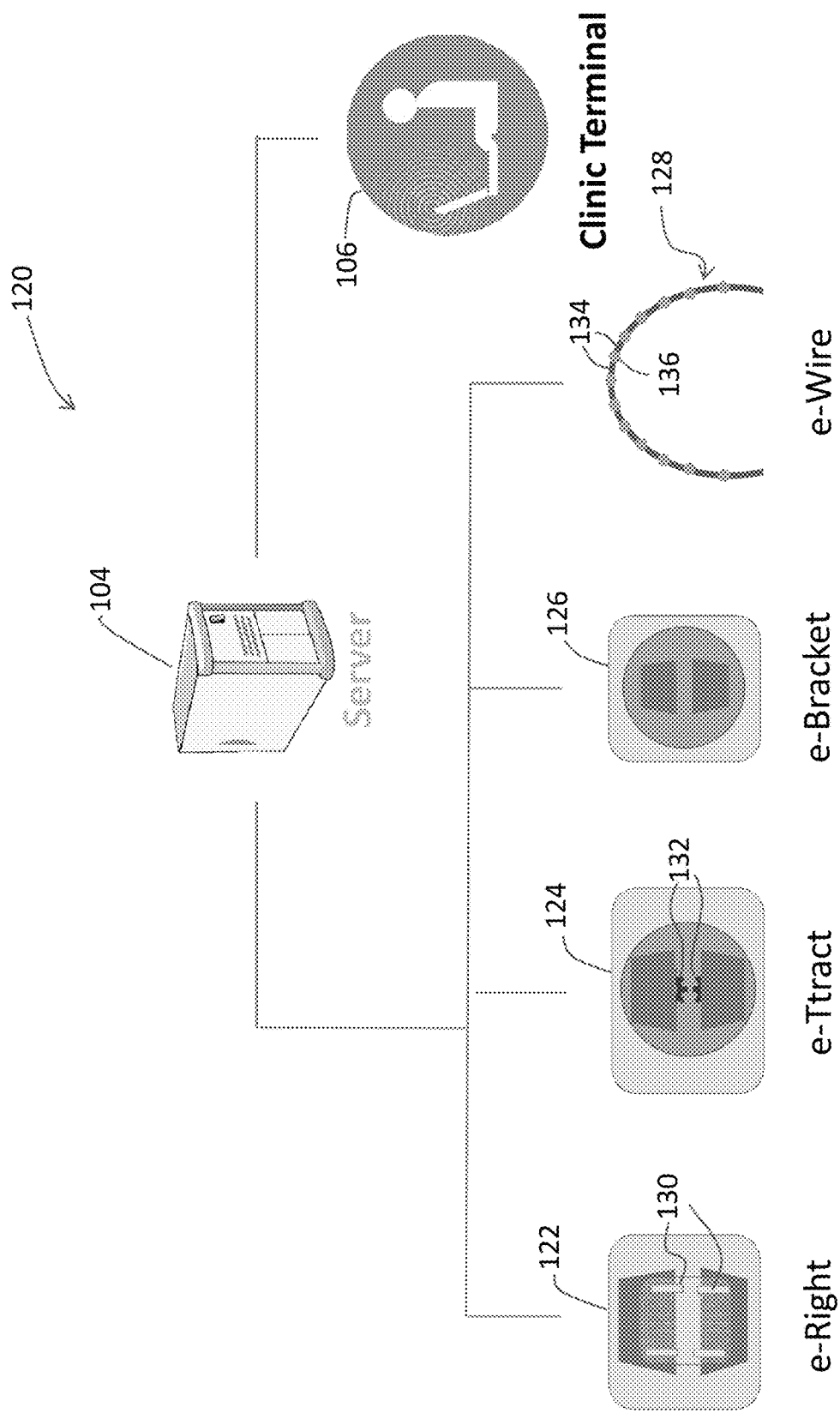
FIG. 2 is a diagram of various modules of the remote orthodontic system.

Referring to FIG. 2, a remote orthodontics system 120 may include a server 104 that communicates with different types of smart orthodontic braces, or orthodontic braces that include more than one type of smart brackets (individually or as a group). The computer server 104 may execute an orthodontic treatment program that is configured to control the various types of braces having various types of smart brackets. The server 104 may communicate with a clinic terminal 106 to enable an orthodontist to remotely monitor treatment progress or provide adjustments.

For example, one type of smart bracket is bracket 122, referred to as the e-Right bracket. The e-Right bracket 122 includes miniature motors that drive miniature gears, which in turn drive small rods 130 that push against an arch wire inserted into a slot of a bracket attached to a tooth. The small rods 130 provide forces that in combination produce the desired amount of force in the desired direction that is applied to the corresponding tooth to provide the required movement for alignment of the tooth.

A second type of smart bracket is bracket 124, referred to as the e-Tract bracket. The e-Tract bracket has two miniature motors that drive miniature gears 132, which in turn pull or push an arch wire (inserted in between) to generate retracting or protracting forces for movement and/or alignment of the corresponding tooth (or a group of teeth).

A third type of smart bracket is bracket 126, referred to as the e-Bracket in this document. The e-Bracket has one or more miniature motors that drive one or more miniature gears, which in turn drive a rotatable base to provide torque to the bracket 126 for generating a force for alignment of the corresponding tooth.

A fourth type of orthodontic braces variation is e-Wire braces 128. The e-Wire braces 128 include arch wire segments 134 connected to smart brackets 136 in which each bracket 136 has one or more miniature motors that apply forces to the arch wire segments 134, such that the interaction of the brackets 136 and wire segments 134 result in the proper amount of forces being applied to the teeth that need adjustment. Each arch wire segment is attached to the corresponding tooth surface in order to translate the delivered force. A patient may use any configuration of two or more of the e-Right bracket 122, e-Tract bracket 124, e-Bracket 126, or e-Wire braces 128 at the same time. The following describes details of the e-Wire braces 128.

Figure 3B:
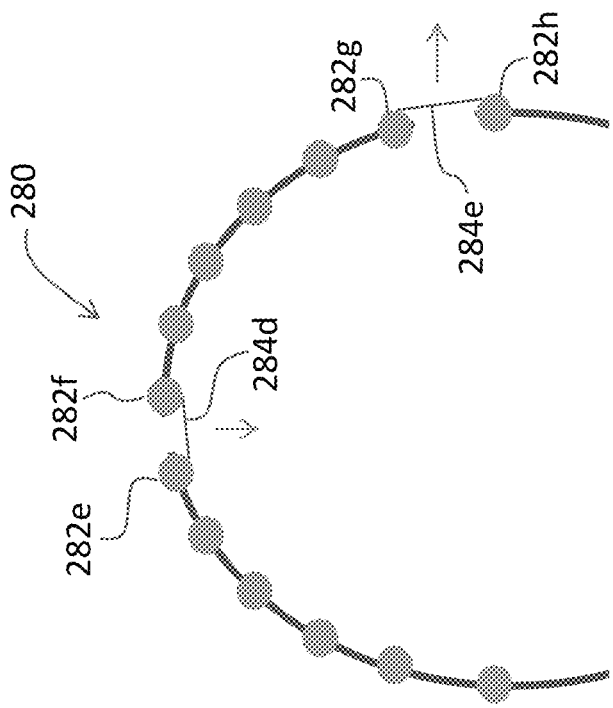
FIGS. 3A and 3B are diagrams of an exemplary e-Wire smart orthodontic wire.
Figure 3A:
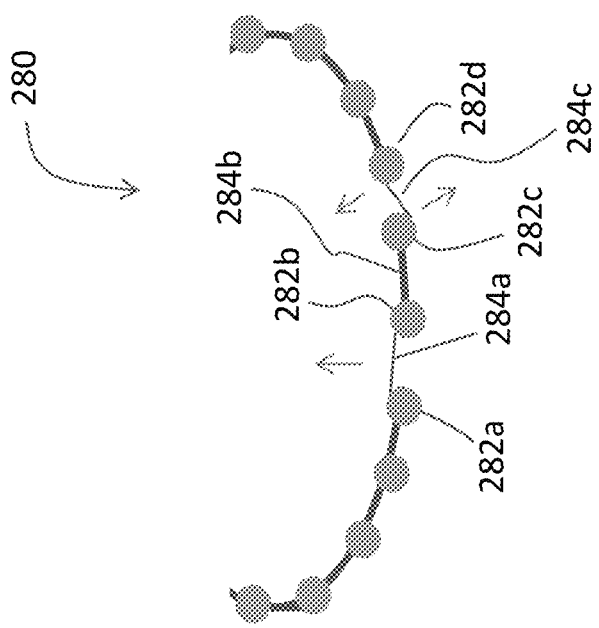

In some implementations, an arch wire is segmented into individual units (for each tooth) and interlinked via smart brackets, joints, or nodes that have the ability to revolve three-dimensionally to provide a detailed movement scheme for each tooth. FIG. 3A shows a front perspective view of an e-Wire smart orthodontic wire 280. FIG. 3B shows an upper view of the smart orthodontic wire 280. The smart orthodontic wire 280 includes smart nodes (e.g., 282a to 282d, collectively 282) and wire segments (e.g., 284a to 284c, collectively 284) between the nodes 282. Each smart node 282 can push or pull an adjacent wire segment in a forward, backward, upward, and/or downward direction with a twisting capability. In this document, depending on context, the smart nodes are also referred to as smart orthodontic brackets.

Two adjacent nodes can push the wire segment between the nodes in the same or different directions. For example, as shown in FIG. 3A, nodes 282a and 282b both push the wire segment 284a in an upward direction. The node 282c pushes one end of the wire segment 284c downward, while the node 282d pushes the other end of the wire segment 284c upward (known as a second order bend action). For example, as shown in FIG. 3B, nodes 282e and 282f both push the wire segment 284d in an inward direction. The nodes 282g and 282h both push the wire segment 284e in an outward direction (known as a first order bend action).

In some implementations, the wire segments 284 are coupled to orthodontic brackets similar to the way that an arch wire is attached to the orthodontic brackets. In other implementation the wire segments 284 can be directly bonded to the tooth surface. Because the nodes and wire segments are connected eventually to a tooth, the force that a node exerts against a wire segment will influence the tooth's final position. Furthermore, the system allows for spontaneous adjustment resulting from interactions between the nodes and the continuous arch wire configuration. For example, the force generated by the node 282a pulling the wire segment 284a may influence the force that is applied to the wire segment 284c, which is transferred to a corresponding bracket and its associated tooth.

Referring to FIG. 4, a smart node 282 has a wire segment attachment extending on each side that can be controlled independently to induce (along with the force provide by the adjacent node) a desired tooth movement. The positional corrections are performed through, e.g., wire twisting (root torque), opposite vertical movement (tilting), and opposite horizontal movement (rotational correction).

Referring to FIG. 5A, the smart node 282 includes a gear module that generates forces that are applied to archwire segments (e.g., 284a and 284b). The gear module can be driven manually or by miniature motors. The following describes examples in which the gear module is driven by miniature motors. In some implementations, the smart node 282 includes a first miniature motor 290 that generates a twisting force on a frame 298 that is connected to the wire segment 284b. The miniature motor 290 also generates a twisting force on a frame 300 that is connected to the wire segment 284a. When a single motor 290 is used, the twisting force applied to the frame 298 is the same as the twisting force applied to the frame 300. In some implementations, two motors can be used so that the twisting force applied to the frame 298 is independent of the twisting force applied to the frame 300, and the twisting force applied to the wire segment 284b is independent of the twisting force applied to the wire segment 284a. The motor 290 can, e.g., drive a transmission link 294 that is coupled to the frame 298, and drive a transmission link 296 that is coupled to the frame 300. Each of the transmission links 295 and 297 may include one or more miniature gears and/or miniature belts. Other ways of transferring the driving force from the motor to the frames 298, 300 can also be used.

A second motor 292 drives a rod 302 that pushes against the frame 300 to push the wire segment 284a inward or outward (i.e., in a direction into the mouth or in a direction out of the mouth). The motor 292 also drives a rod 304 that pushes against the frame 298 to push the wire segment 284b inward or outward. When two motors are used, the movement of the rod 302 is independent of the movement of the rod 304, so the inward or outward movements of the segments 284a and 284b can be independent of each other. A third motor (not shown in the figure) provides a force for rotating the node 282 or moving the rods 302 and 304 in directions perpendicular to those described above (e.g., producing upward and/or downward movements).

Figure 5B:
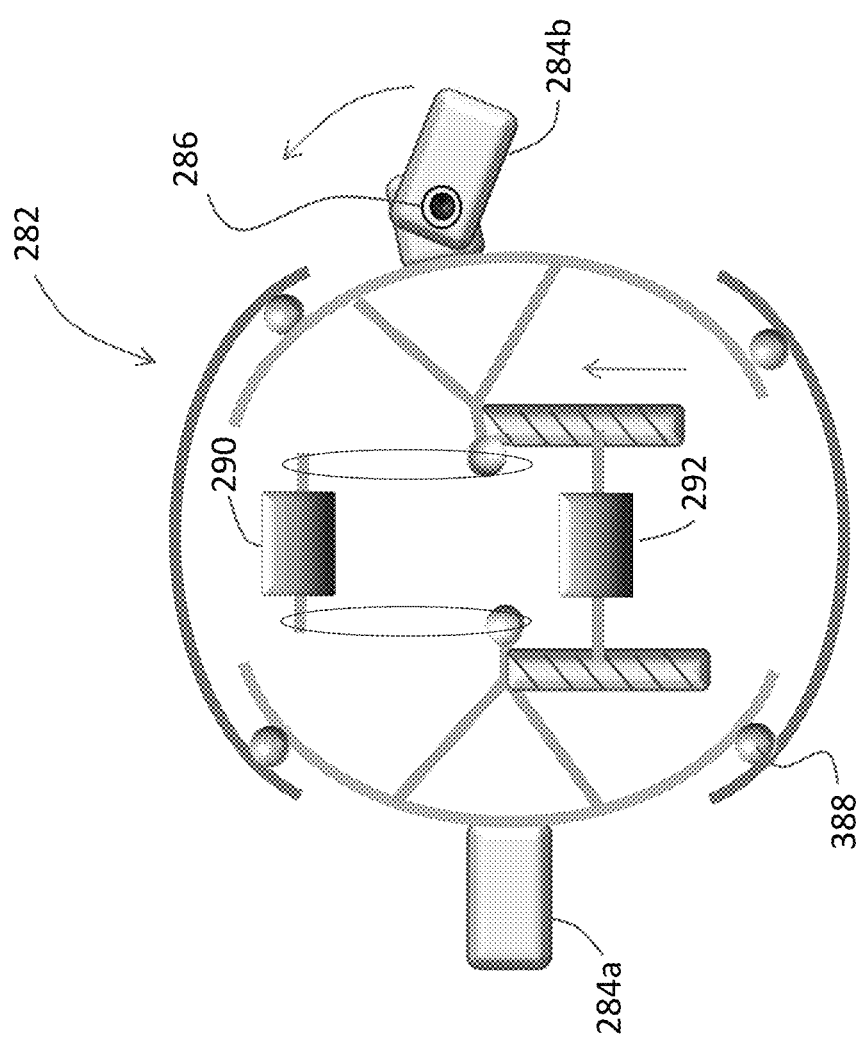

FIG. 5B shows a vertical cross-sectional view of the smart node 282 when the lower motor 292 is activated to achieve second-order action (i.e., tilting one end). The upper motor 290 when activated causes twisting action of the wire segment 284b (i.e., third-order action to cause root torquing or movement). In some implementations, a first end of the wire segment 284b is connected to a first smart node 282 via a rotational joint 286. A second end (not shown in the figure) of the wire segment 284b is connected to a second smart node (not shown in the figure) via another rotational joint. This allows the first smart node 282 and the second smart node to move independently even though the first smart node 282 and the second smart node are both joined to the same wire segment 284b. For example, the miniature motor 290 in the first smart node 282 may cause the first end of the wire segment 284b to move up (as shown in FIG. 5B), while the second smart node causes the second end of the wire segment 284b to move down (as shown in the example of FIG. 3A).

Figure 5C:
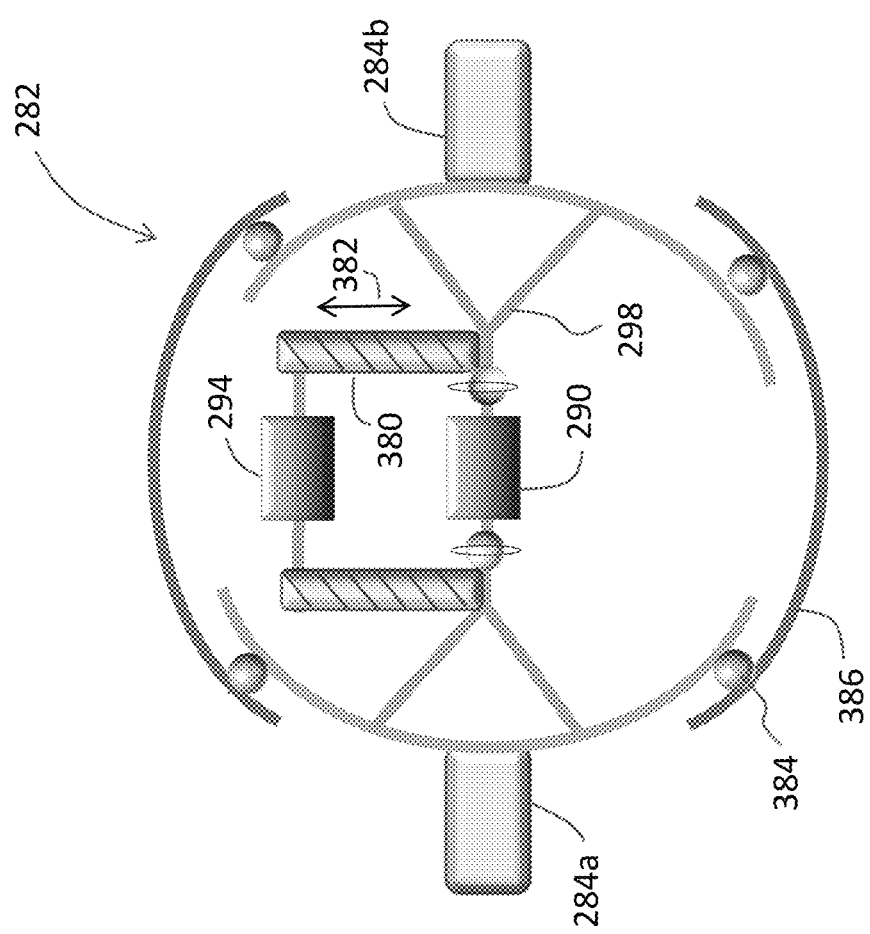

FIG. 5C shows a horizontal cross-sectional view of the smart node 282. A third motor 294 controls the in-out movement (first-order action) of the wire segments 284a and 284b. When the motor 294 drives a rod 380 to move along a direction 382, the rod 382 pushes the bracket 298 to cause the wire segment 284b to have a movement in the labial or lingual direction. In FIG. 5C, the motor 292 is below the motor 290 and is blocked from view. The smart node 282 includes four sliding metal balls 384 to enable the bracket 298 to slide against an outer frame 386. There are also four sliding metal balls 388 in the vertical cross-sectional view of FIG. 5B. Thus, in this example, there are a total of eight sliding metal balls.

Figure 5D:
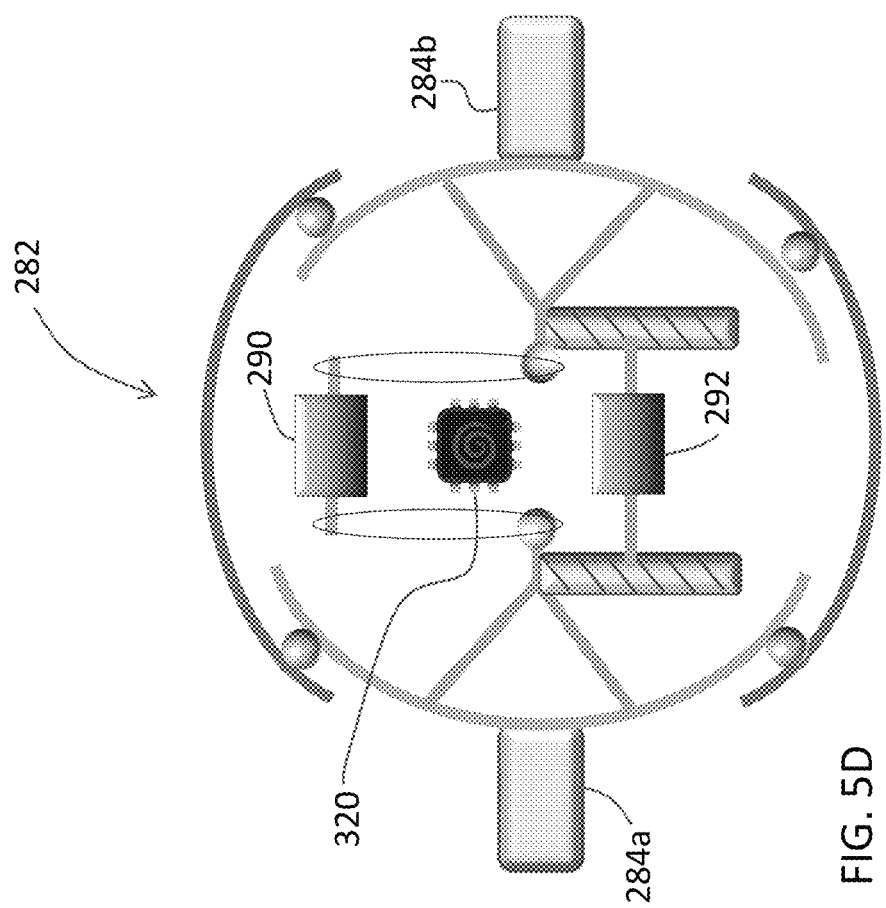

Referring to FIG. 5D, in some implementations, the smart node 282 includes an integrated circuit chip 320 that has circuitry for controlling the miniature motors (e.g., 290, 292, 294). The integrated circuit chip 320 has circuitry for communicating wirelessly to external devices, such as the reader 108 or the cell phone 110.

Referring to FIG. 5E, in some implementations, a smart node 374 can have miniature gears in gear boxes 370 and 372 that can be driven manually using mini-screws that extend to external of the smart node 374 such that the screw heads are accessible to a user. For example, mini-screws 340, 342, 344, 346 can be driven manually by the user to move the frames 298 and 300. For example, the screw 340 drives a gear that drives the transmission link 295 that is coupled to the frame 298 and can cause the frame 298 to rotate. The screw 342 drives a gear that drives the transmission link 297 that is coupled to the frame 300 and can cause the frame 300 to rotate. The screw 344 drives a gear that drives the rod 304 that is coupled to the frame 298 and can cause the frame 298 to move up or down. The screw 346 drives a gear that drives the rod 302 that is coupled to the frame 300 and can cause the frame 300 to move up or down.

In the example of FIG. 5E, the smart node 374 includes six mini-screws (two for each gearbox—only four mini-screws are shown in the figure), controlling the variable and all possible tooth movements (first, second, and third order movements), on each side of the node independently. For example, the screw heads can be positioned at the superior, inferior, and frontal aspects of the node 374 so that they are accessible to the user.

Figure 6:
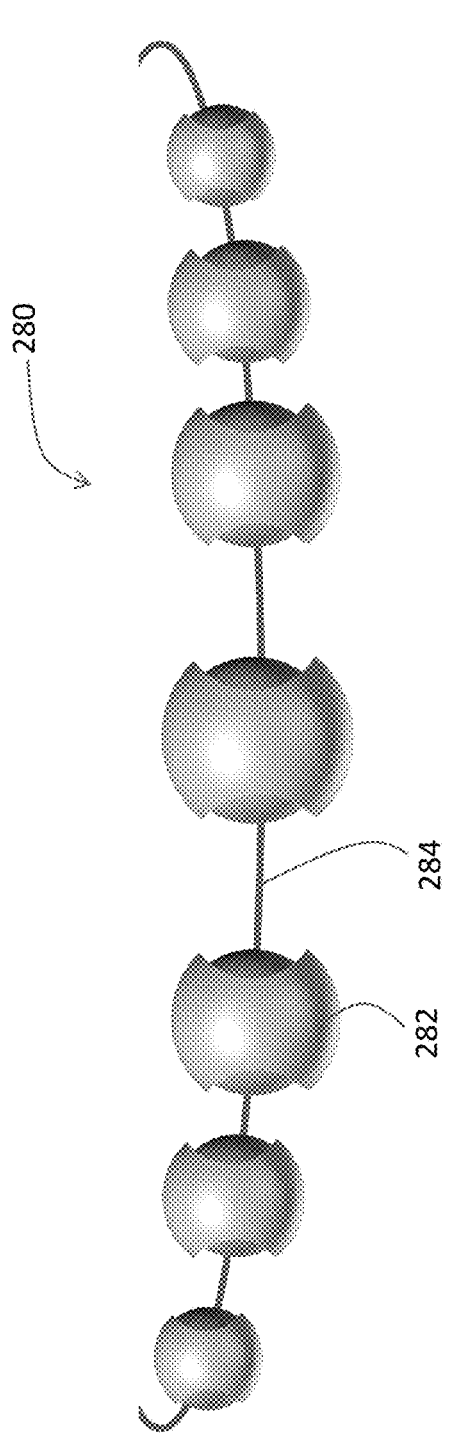
FIG. 6 shows a front view of the e-Wire smart orthodontic wire.
Figure 7A:
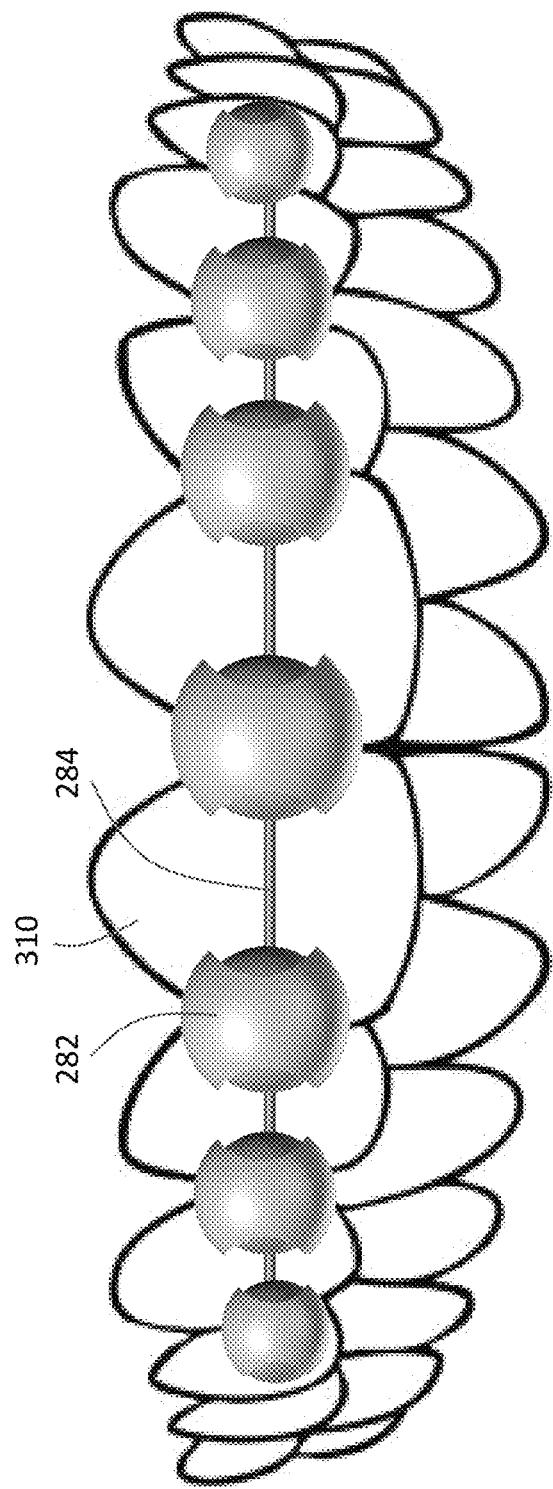
FIGS. 7A and 7B show diagrams of the position of the e-Wire smart orthodontic wire relative to a user's teeth.
Figure 7B:
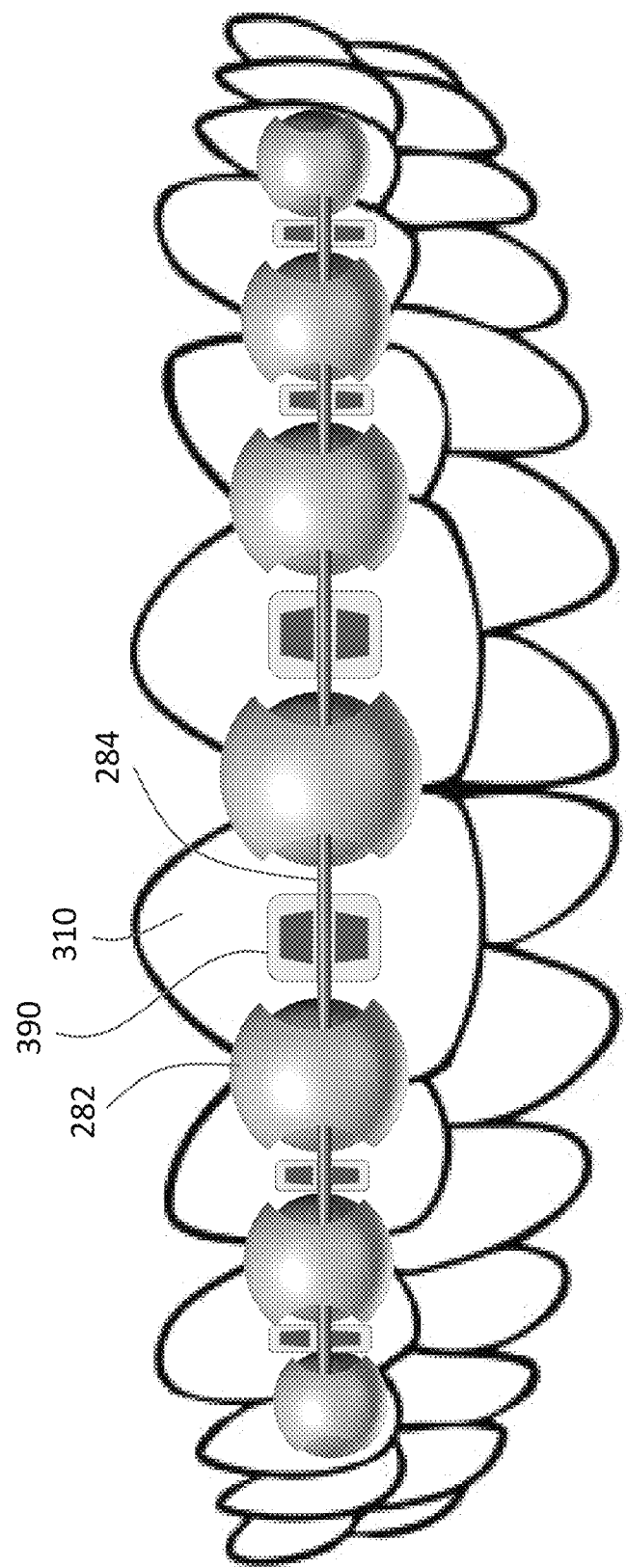

FIG. 6 shows a front view of the e-Wire smart orthodontic wire 280. FIG. 7A shows the smart orthodontic wire 280 positioned relative to the teeth. Referring to FIG. 7B, in some examples, each of the wire segments 284 between two smart nodes 282 is coupled to a bracket 390 that is attached to a corresponding tooth 310. For example, the wire segment 284 can be inserted into an archwire slot of the bracket. The bracket 390 can be either a traditional orthodontic bracket or a smart bracket that can provide adjustable forces to the wire segment. In some examples, each of the wire segments 284 can be attached to the corresponding tooth by other interfaces, or by directly gluing the wire segment to a treated tooth surface.

Figure 8:
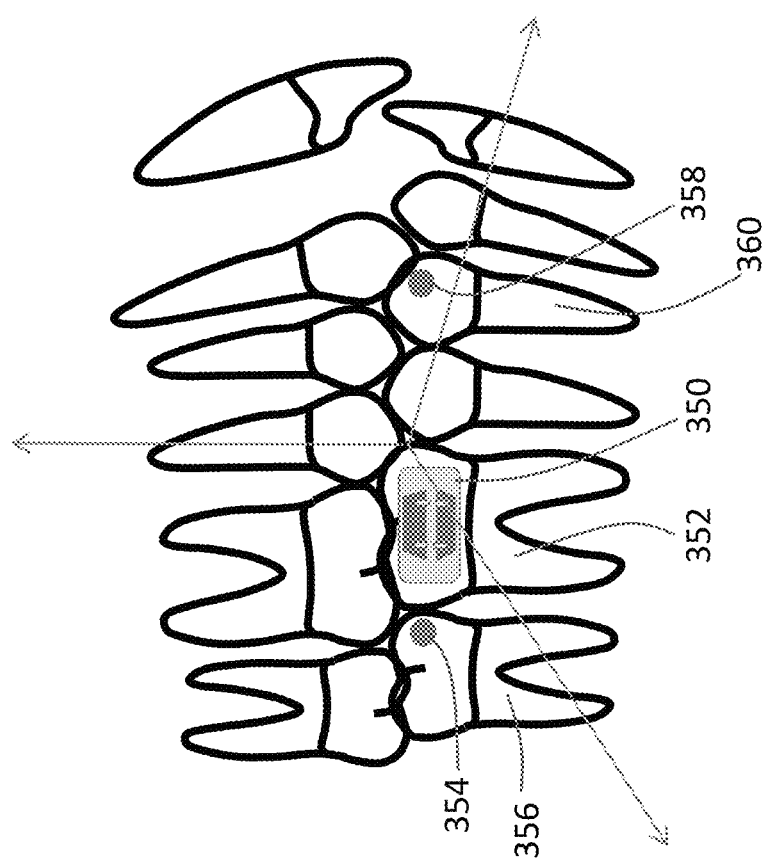
FIG. 8 is a diagram of a smart bracket and exemplary reference markers.

Various smart orthodontic brackets and wires have been described above. These smart brackets and wires can be used in the remote orthodontic system 100 of FIG. 1. Referring to FIG. 8, in order to monitor the movement of the tooth under treatment, markers can be attached to one or more adjacent teeth. For example, a bracket 350 is attached to a tooth 352 that needs to be aligned. A first marker 354 is attached to a tooth 356, and a second marker 358 is attached to another tooth 360. When the bracket 350 is first installed on the tooth 352, a set of one or more pictures of the teeth are taken. After a period of time, such as three or four weeks later, a second set of one or more pictures of the teeth are taken. The movement of the tooth 352 under treatment relative to the other teeth 356 and 360 can be measured by comparing the position of the bracket 350 relative to the markers 354 and 358 that function as reference points.

In some examples, the patient takes images of the teeth and sends them to the orthodontist, who monitors the progress of the treatment. If the movement of the tooth 352 is according to plan, then the e-Wire smart orthodontic wire 280 will be adjusted according to plan. After adjustment, the e-Wire smart orthodontic wire 280 will provide the appropriate forces to the wire segments, which in turn provide appropriate forces to the orthodontic brackets coupled to the wire segments. If the movement of the tooth 352 is outside of acceptable boundaries, then the orthodontist may adjust the treatment plan or ask the patient to return to the clinic for further examination and/or treatment. When the orthodontist needs to adjust the treatment plan, the orthodontist may send an instruction from the clinic terminal 106 to the server computer 104 to adjust the treatment plan stored locally at the server 104.

In some examples, the mobile phone 110 may execute an orthodontic app that provides instructions to the patient or a helper of the patient on how to take pictures in order to accurately determine the movement of the tooth 352. For example, a helper may use the camera on the mobile phone 110 to take pictures of the patient's teeth. A reference image that was previously taken can be overlaid on a live view taken by the phone camera. The reference image may show the two markers 354 and 358, so that the helper may position and orient the camera to take a picture of the teeth in which the markers 354 and 358 are at similar positions in the new picture. This makes it easier to compare the current picture with a previously taken picture to determine the movement of the tooth 352. A set of orthodontic biomechanical algorithms can be used by the system 100 to determine the auto adjustments to be made to the smart orthodontic wire 280, such as increasing or decreasing the forces applied to the wire segments by the e-Wire smart orthodontic wire 280.

The brackets used with the smart orthodontic wire 280 may be smart brackets that have sensors for sensing the force applied to the corresponding tooth. For example, a microelectromechanical sensor system having piezoresistive microsensors attached between the smart bracket and the tooth can be used to take measurements that can be used to calculate forces applied to the tooth in the x, y, and z directions, and moments in the x, y, and z directions. By monitoring the forces actually applied to the tooth, the system 100 can determine whether the motors in the smart nodes need to be adjusted to apply more or less force in a certain direction.

The chip 320 (FIG. 5D), the miniature motors, and the sensors system can be powered wirelessly by beaming power to microcoils in the smart nodes. The chip 320 may include circuitry for modulating data sent to the reader 108 or the server 104, or demodulating the signals sent from the reader 108 or the server 104.

The remote orthodontic system 100 helps orthodontists and their patients to have a high quality orthodontic treatment, with reduced visits to the dental office and reduced costs. For example, the adjustments to the smart brackets and arch wires can be made while the patients are at home. The orthodontists can also monitor the treatments and make adjustments to the treatment plans from home, allowing more flexible work schedules.

A novel smart orthodontic wire having brackets or nodes that can generate and deliver forces to wire segments has been described above. The system 100 is interactive in which the patient and the treatment provider are able to monitor the status of teeth alignment and report responses and symptoms. The system can be remotely controlled, enabling quick re-adjustment and auto-correction. The system can apply biomechanical equations based on the known static and dynamic equilibrium laws and algorithms. The system provides treatments with predictable and improved outcomes, so the treatment duration can be accurately forecasted and better controlled.

Each of the computer server 104, mobile phone 110, and reader 108 can include one or more processors and one or more computer-readable mediums (e.g., RAM, ROM, SDRAM, hard disk, optical disk, and flash memory). The one or more processors can perform various calculations or control functions described above. The calculations and various functions can also be implemented using application-specific integrated circuits (ASICs). The term "computer-readable medium" refers to a medium that participates in providing instructions to a processor for execution, including without limitation, non-volatile media (e.g., optical or magnetic disks), and volatile media (e.g., DRAM) and transmission media. Transmission media includes, without limitation, coaxial cables, copper wire and fiber optics.

The features described above can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language (e.g., C, Java), including compiled or interpreted languages, and it can be deployed in any form, including as a stand-alone program or as a module, component, subroutine, a browser-based web application, or other unit suitable for use in a computing environment.

Suitable processors for the execution of a program of instructions include, e.g., both general and special purpose microprocessors, digital signal processors, and the sole processor or one of multiple processors or cores, of any kind of computer. Generally, a processor will receive instructions and data from a read-only memory (ROM) or a random access memory (RAM) or both. The essential elements of a computer are a processor for executing instructions and one or more memories for storing instructions and data. Generally, a computer will also include, or be operatively coupled to communicate with, one or more mass storage devices for storing data files. The mass storage devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM, CD-R, DVD-ROM, DVD-R, Blu-ray DVD disks. The processor and the memory can be supplemented by, or incorporated in, ASICs (application-specific integrated circuits). The chip 320 (FIG. 5D) may include one or more processors described above. The chip 320 may also include one or more volatile or non-volatile memories for storing instructions to be executed by the one or more processors.

While this specification contains many specific implementation details, these should not be construed as limitations on the scope of any inventions or of what may be claimed, but rather as descriptions of features specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

Other embodiments are within the scope of the following claims. For example, a combination of various types of smart brackets can be used for treating one patient. The smart brackets and arch wires can be made of materials different from those described above. In some implementations, each smart node can include a radio frequency identification tag associated with a unique identifier. In some implementations, each chip (e.g., 320) has a unique identifier. This way, if a patient has multiple smart nodes, the server 104 can uniquely identify each smart node and send different instructions to different smart nodes.

What is claimed is:

1. An orthodontic appliance, comprising:
   a first module having a mesial end and a distal end;
   a second module having a mesial end and a distal end;
   a first archwire segment coupled to the distal end of the first module;
   a second archwire segment coupled between the mesial end of the first module and the distal end of the second module, in which the second archwire segment is not directly connected to the first archwire segment; and
   a third archwire segment coupled to the mesial end of the second module, in which the third archwire segment is not directly connected to the second archwire segment;
   wherein the orthodontic appliance is configured to be attached to teeth
   wherein the first module has a first gear system, the second module has a second gear system, and the first and second gear systems are configured to move the second archwire segment relative to the first and second modules.

2. The orthodontic appliance of claim 1 in which the first gear system is configured to apply a first force to a first end of the second archwire segment along a lingual-facial direction.

3. The orthodontic appliance of claim 2 in which the second gear system is configured to apply a second force to a second end of the second archwire segment along a lingual-facial direction.

4. The orthodontic appliance of claim 2 in which the second gear system is configured to apply a second force to a second end of the second archwire segment along an occlusal-gingival direction.

5. The orthodontic appliance of claim 1 in which the first gear system is configured to apply a force to an end of the second archwire segment along an occlusal-gingival direction.

6. The orthodontic appliance of claim 1 in which the first gear system is configured to apply a first rotational force to a first end of the second archwire segment.

7. The orthodontic appliance of claim 6 in which the second gear system is configured to apply a second rotational force to a second end of the second archwire segment.

8. The orthodontic appliance of claim 1 in which the first gear system is configured to be driven manually, the first gear system transmitting a manual force to a first end of the second archwire segment.

9. The orthodontic appliance of claim 8 in which the second gear system is configured to be driven manually, the second gear system transmitting a manual force to a second end of the second archwire segment.

10. The orthodontic appliance of claim 1 in which the first module comprises a first miniature motor configured to drive the first gear system to generate a first force that is applied to a first end of the second archwire segment.

11. The orthodontic appliance of claim 10 in which the second module comprises a second miniature motor configured to drive the second gear system to generate a second force that is applied to a second end of the second archwire segment.

12. The orthodontic appliance of claim 10, comprising a wireless energy transfer module to receive energy wirelessly for powering the first miniature motor.

13. The orthodontic appliance of claim 10, comprising an integrated circuit having circuitry to control the first miniature motor.

14. The orthodontic appliance of claim 13 in which the integrated circuit comprises a communication module to communicate wirelessly with an external device.

15. The orthodontic appliance of claim 14 in which the integrated circuit is configured to receive instructions wirelessly and control the first motor according to the instructions.

16. The orthodontic appliance of claim 1, further comprising a bracket having a base configured to be attached to a surface of a tooth, the bracket defining an archwire slot configured to receive the second archwire segment.

17. The orthodontic appliance of claim 16, comprising a sensor to detect a force applied by the bracket to the tooth.

18. The orthodontic appliance of claim 17, comprising a wireless energy transfer module to receive energy wirelessly for powering the sensor.

19. The orthodontic appliance of claim 1 in which the first module comprises a radio frequency identification tag associated with a unique identifier.

20. The orthodontic appliance of claim 1 in which the first module comprises a first frame that is coupled to the second archwire segment, and the first gear system is configured to apply a force to the first frame, which in turn applies the first force to the second archwire segment.

21. The orthodontic appliance of claim 20 in which the first gear system comprises a miniature motor that is configured to generate the force applied to the first frame.

22. The orthodontic appliance of claim 21, comprising a wireless energy transfer module to receive energy wirelessly for powering the miniature motor.

23. The orthodontic appliance of claim 21, comprising an integrated circuit having circuitry to control the miniature motor.

24. The orthodontic appliance of claim 23 in which the integrated circuit comprises a communication module to communicate wirelessly with an external device.

25. The orthodontic appliance of claim 24 in which the integrated circuit is configured to receive instructions wirelessly and control the miniature motor according to the instructions.

26. The orthodontic appliance of claim 20 in which the first gear system comprises a gear that is configured to be driven manually by a user to generate the force applied to the first frame.

27. The orthodontic appliance of claim 20 in which the second module comprises a second frame that is coupled to the second archwire segment, and the second gear system is configured to apply a force to the second frame, which in turn applies a force to the second archwire segment.

28. The orthodontic appliance of claim 1, comprising a first orthodontic bracket configured to be attached to a first tooth, the first orthodontic bracket defining an archwire slot for receiving the first archwire segment and enabling a first force applied by the first gear system to the first archwire segment to be transmitted to the first orthodontic bracket through the first archwire segment.

29. The orthodontic appliance of claim 28, comprising a sensor to detect a force applied by the first orthodontic bracket to the first tooth.

30. The orthodontic appliance of claim 29, comprising a wireless energy transfer module to receive energy wirelessly for powering the sensor.

31. The orthodontic appliance of claim 28, comprising:
a second orthodontic bracket configured to be attached to a second tooth,
the second orthodontic bracket defining an archwire slot for receiving the second archwire segment and enabling a second force applied by the first and second gear systems to the second archwire segment to be transmitted to the second orthodontic bracket through the second archwire segment.

32. The orthodontic appliance of claim 1 in which the first gear system comprises a base, a first gear, and a first coupling member, the first coupling member being coupled to a first end of the first archwire segment, and the first gear is configured to move the first coupling member relative to the base.

33. The orthodontic appliance of claim 32 in which the first gear system comprises a second gear and a second coupling member, the second coupling member being coupled to a first end of the second archwire segment, and the second gear is configured to move the second coupling member relative to the base.

34. The orthodontic appliance of claim 1 in which the first gear system is configured to apply a first force to a first end of the first archwire segment along a lingual-facial direction.

35. The orthodontic appliance of claim 34 in which the first gear system is configured to apply a second force to a first end of the second archwire segment along a lingual-facial direction.

36. The orthodontic appliance of claim 34 in which the first gear system is configured to apply a second force to a first end of the second archwire segment along an occlusal-gingival direction.

37. The orthodontic appliance of claim 1 in which the first gear system is configured to apply a first force to a first end of the first archwire segment along an occlusal-gingival direction.

38. The orthodontic appliance of claim 1 in which the first gear system comprises a base, a first gear, and a first coupling member, the first coupling member being coupled to a first end of the first archwire segment, and the first gear is configured to rotate the first coupling member relative to the base along a first direction.

39. The orthodontic appliance of claim 38, wherein the second archwire segment has a first end coupled to the first module, and the first gear system is also configured to generate a second force that is applied to the first end of the second archwire segment, wherein the first gear system comprises a second gear and a second coupling member, the second coupling member being coupled to the first end of the second archwire segment, and the second gear is configured to rotate the second coupling member relative to the base along a second direction.

40. The orthodontic appliance of claim 1,
wherein the second archwire segment is coupled to the first module through a first rotating joint; and
wherein the first gear system is configured to move the second archwire segment relative to the first module.

41. The orthodontic appliance of claim 40 in which the first gear system is configured to apply a first force to a first end of the second archwire segment along a lingual-facial direction.

42. The orthodontic appliance of claim 41, in which a first end of the second archwire segment is coupled to the first module through the first rotating joint and a second end of the second archwire segment is coupled to the second module through a second rotating joint.

43. The orthodontic appliance of claim 42 in which the second gear system is configured to apply a second force to the second end of the second archwire segment along a lingual-facial direction.

44. The orthodontic appliance of claim 42 in which the second gear system is configured to apply a second force to the second end of the second archwire segment along an occlusal-gingival direction.

45. The orthodontic appliance of claim 40 in which the first gear system is configured to apply a force to an end of the second archwire segment along an occlusal-gingival direction.

46. The orthodontic appliance of claim 40 in which the first gear system is configured to apply a first rotational force to a first end of the second archwire segment.

47. The orthodontic appliance of claim 46, in which a first end of the second archwire segment is coupled to the first module through the first rotating joint and a second end of the second archwire segment is coupled to the second module through a second rotating joint, and the second gear system is configured to apply a second rotational force to the second end of the second archwire segment.

48. The orthodontic appliance of claim 40 in which the first gear system is configured to be driven manually, the first gear system transmitting a manual force to a first end of the second archwire segment.

49. The orthodontic appliance of claim 48, in which a first end of the second archwire segment is coupled to the first module through the first rotating joint and a second end of the second archwire segment is coupled to the second module through a second rotating joint, the second gear system is configured to be driven manually, and the second gear system is configured to transmit a manual force to the second end of the second archwire segment.

50. The orthodontic appliance of claim 40 in which the first module comprises a first miniature motor configured to drive the first gear system to generate a first force that is applied to a first end of the second archwire segment.

51. The orthodontic appliance of claim 50, in which a first end of the second archwire segment is coupled to the first module through the first rotating joint and a second end of the second archwire segment is coupled to the second module through a second rotating joint, the second module comprises a second miniature motor configured to drive the second gear system to generate a second force that is applied to the second end of the second archwire segment.

52. The orthodontic appliance of claim 50, comprising a wireless energy transfer module to receive energy wirelessly for powering the first miniature motor.

53. The orthodontic appliance of claim 50, comprising an integrated circuit having circuitry to control the first miniature motor.

54. The orthodontic appliance of claim 53 in which the integrated circuit comprises a communication module to communicate wirelessly with an external device.

55. The orthodontic appliance of claim 54 in which the integrated circuit is configured to receive instructions wirelessly and control the first miniature motor according to the instructions.

56. The orthodontic appliance of claim 40, further comprising a bracket having a base configured to be attached to a surface of a tooth, the bracket defining an archwire slot configured to receive the second archwire segment.

57. The orthodontic appliance of claim 56, comprising a sensor to detect a force applied by the bracket to the tooth.

58. The orthodontic appliance of claim 57, comprising a wireless energy transfer module to receive energy wirelessly for powering the sensor.

59. The orthodontic appliance of claim 40 in which the first module comprises a radio frequency identification tag associated with a unique identifier.

60. A method for orthodontic treatment
coupling a first archwire segment to a distal end of a first gear module;
coupling a second archwire segment between a mesial end of the first gear module and a distal end of a second gear module;
coupling a third archwire segment to a mesial end of the second gear module; to form an orthodontic appliance configured to be attached to teeth and
driving gears in the first and second gear modules to apply forces to move the second archwire segment relative to the first and second gear modules;
wherein the first, second, and third archwire segments are individual archwire segments that do not form a continuous archwire.

61. The method of claim 60, comprising applying a first force to a first end of the second archwire segment along a lingual-facial direction.

62. The method of claim 61, comprising applying a second force to a second end of the second archwire segment along a lingual-facial direction.

63. The method of claim 61, comprising applying a second force to a second end of the second archwire segment along an occlusal-gingival direction.

64. The method of claim 60, comprising applying a first force to an end of the second archwire segment along an occlusal-gingival direction.

65. The method of claim 60, comprising applying a first rotational force to a first end of the second archwire segment.

66. The method of claim 65, comprising applying a second rotational force to a second end of the second archwire segment.

67. The method of claim 60 in which driving gears comprises manually driving the gears.

68. The method of claim 60 in which driving gears comprising using one or more miniature motors to drive the gears.

69. The method of claim 68, comprising transmitting energy wirelessly to a wirelessly energy transfer module to power the one or more motors.

70. The method of claim 68, comprising operating an integrated circuit to control the one or more miniature motors.

71. The method of claim 70, comprising, at the integrated circuit, communicating wirelessly with an external device.

72. The method of claim 71, comprising, at the integrated circuit, receiving instructions wirelessly and controlling the one or more miniature motors according to the instructions.

73. The method of claim 60, comprising attaching a bracket to a surface of a tooth, and passing the second archwire segment through an archwire slot defined by the bracket.

74. The method of claim 73, comprising using a sensor to sense a force applied by the bracket to the tooth.

75. The method of claim 74, comprising transferring energy wirelessly to a wirelessly energy transfer module to power the sensor.

76. The method of claim 60, comprising probing a radio frequency identification tag attached to the first gear module to determine a unique identifier.

* * * * *